United States Patent [19]
Sillard

[11] Patent Number: 5,246,368
[45] Date of Patent: Sep. 21, 1993

[54] METHOD FOR MANUFACTURE AND FITTING OF PARTIAL DENTAL APPLIANCE

[76] Inventor: Rannar Sillard, 206 Madison Ave., Lakewood, N.J. 08701

[21] Appl. No.: 18,276

[22] Filed: Jan. 22, 1993

[51] Int. Cl.[5] .............................. A61C 13/00
[52] U.S. Cl. .................. 433/167; 433/200.1; 433/172
[58] Field of Search .......... 433/167, 172, 200.1, 433/213; 219/69.15; 29/160.6; 164/DIG. 4

[56] References Cited

U.S. PATENT DOCUMENTS 4,627,136 12/1986 Kreylos et al. ............... 29/160.6
4,931,016 6/1990 Sillard ............................ 433/167
5,057,017 10/1991 Sillard ............................ 433/167

Primary Examiner—Cary E. O'Connor
Attorney, Agent, or Firm—Clifford G. Frayne

[57] ABSTRACT

A process for fabricating a partial denture or bridge appliance securable to an abutment tooth or abutment teeth having crowns or copings thereon, the partial denture or bridge appliance in snap fit secure relationship with the crown or coping on the abutment tooth or teeth, the snap-fit fitting achieved by electrical erosion methods in order to eliminate any undue stress or strain on the abutment tooth or teeth so as to prevent their eventual loosening or loss.

2 Claims, 2 Drawing Sheets

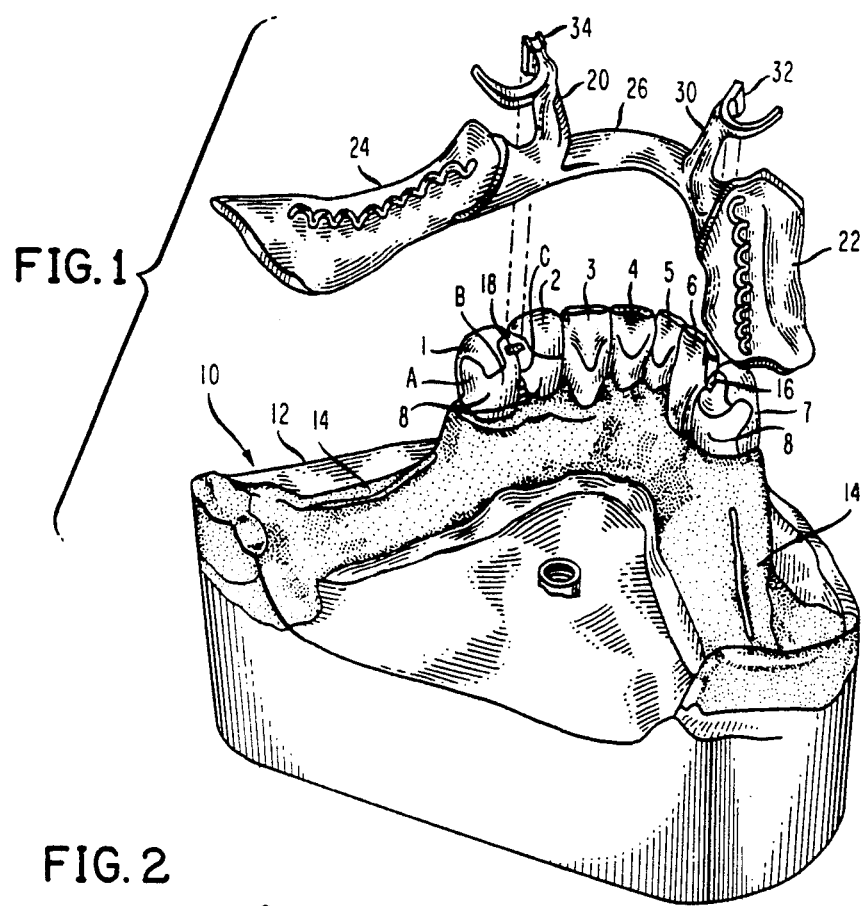
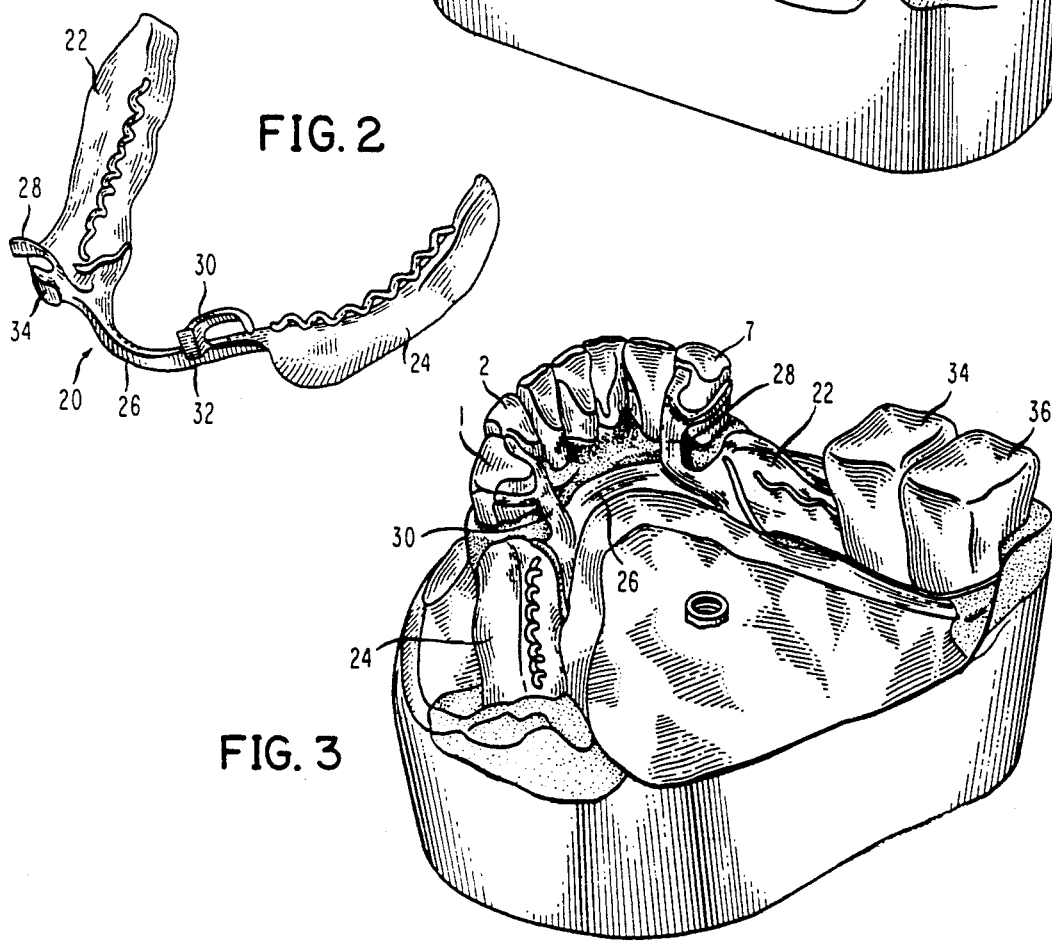
FIG. 1
FIG. 2
FIG. 3

METHOD FOR MANUFACTURE AND FITTING OF PARTIAL DENTAL APPLIANCE

BACKGROUND OF THE INVENTION

1. Field of Invention

The present invention relates to an improved method for the manufacture and fitting of partial denture dental appliances, such as a partial denture, which when secured to the crowned abutment teeth does not create any damaging stress forces to the abutment teeth.

2. Description of the Prior Art

Partial denture dental appliances in the form of partial dentures in order to replace and compensate for lost or damaged teeth are common. In practice, most partial dentures are secured to an abutment tooth for which in most cases is a natural tooth to which a crown or coping has been affixed. The partial denture is secured to this crown or coping by retentive means.

The practice in the past has been to take an impression of the patient's mouth and to cast a partial framework which would be secured to the crown on the abutment tooth in order to maintain the partial denture in position. The difficulty which arises in this method is that slight casting errors can create stresses and strains between the crowned abutment tooth and the saddles of the partial plate. These stresses and strains can serve to cause a loose fit of the partial denture and might quite possibly cause sufficient stress and strain on the abutment tooth that it too would have to be replaced.

Applicant's prior patents, U.S. Pat. Nos. 4,931,016 and 5,057,017 were directed to dental implant systems for securing a denture directly to the alveolar bone.

Applicant has developed a method for the manufacture and fitting of the partial denture dental appliance utilizing electrical discharge machining (EDM) methods which utilize low voltage and low amperage under reversing polarity to fabricate a partial dental appliance which eliminates the possibility of any stress and strain being exerted upon the crowned abutment tooth and results in a more secure and accurate fit.

OBJECTS OF THE INVENTION

An object of the present invention is to provide for a novel and improved method for the manufacture and fitting of a partial denture dental appliance.

A further object of the present invention is to provide for a novel and improved method for fitting a partial dental appliance so as to avoid the stress or strain between the appliance and that of the crowned abutment teeth.

A still further object of the present invention is to provide for a novel and improved method for the manufacture and fitting of a partial denture dental appliance utilizing electrical discharge machining (EDM) methods.

A still further object of the present invention is directed to a novel and improved method for the manufacture and fitting of a partial denture dental appliance in which the locking means between the partial denture dental appliance and the abutment teeth can be located mesial, distal, lingual, interproximal or occlusal.

SUMMARY OF THE INVENTION

A method for manufacture and fitting of a partial denture dental appliance for precision fit to the crowned abutment teeth whereby the metal partial dental appliance is electrically eroded with the metal crown or coping of the abutment teeth to form a precision male/female retentive locking means thereby eliminating any casting error in the preparation of the partial denture dental appliance and eliminating stress or strain between the saddles of the partial denture dental appliance and the crowned abutment teeth. The electrical discharge machining process for locking the partial dental appliance to the crowns or copings of the abutment teeth allows for positioning of the locking means in either the mesial, distal, lingual, or interproximal or occlusal areas of the crowns or copings.

BRIEF DESCRIPTION OF THE DRAWINGS

These and other objects of the present invention will become evident, particularly when taken in light of the following illustration wherein:

FIG. 1 is a perspective, exploded view of a refractory cast of a patient's mouth for which a partial denture dental appliance is to be secured;

FIG. 2 is a perspective view of a partial denture dental appliance;

FIG. 3 is a perspective view of the partial denture dental appliance secured to the refractory cast in a manner as would be secured within the patient's mouth;

DETAILED DESCRIPTION OF THE DRAWINGS

Figure 4:
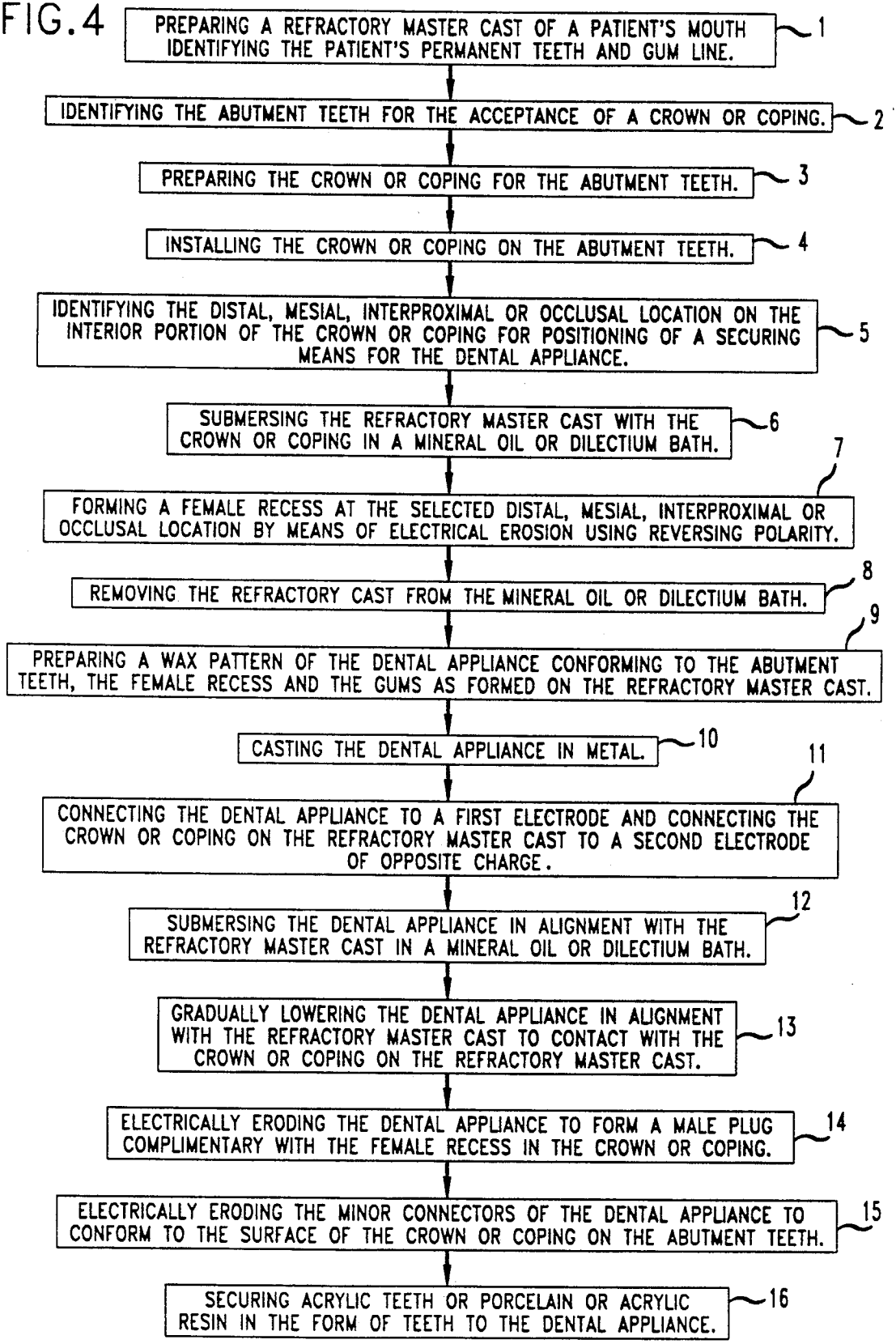
FIG. 4 is a schematic flow chart depicting the process of fabrication of the partial denture dental appliance.

FIG. 1 illustrates a refractory cast of a patient's mouth. The refractory cast 10 is created from an impression made of the patient's mouth by a dentist. The impression of the patient's mouth serves as the mold for the preparation of the refractory cast. The refractory cast identifies the position of the individual's teeth and gum lines.

For purposes of explanation with respect to Applicant's method, the lower jaw of an individual is illustrated in FIG. 1 with respect to refractory cast 10. The base 12 of the refractory cast identifies the individual patient's lower gum line 14 which is supported by the underlying alveolar bone (not shown). As illustrated in FIG. 1, the refractory cast 10 discloses the patient's original seven (7) front teeth identified by reference numerals 1 through 7 consecutively. The remaining teeth from the lower jaw are missing or have been removed which necessitates the preparation of a partial denture dental appliance for the individual patient. It is desirable that the partial denture dental appliance to which the prosthetic teeth will be affixed, will be secured to the existing teeth in a manner which is both aesthetically pleasing, and which also maintains the partial denture dental appliance in a secure position without resulting in any undue stress or strain influence on the existing teeth which might lead to their eventual loosening and loss.

In past practice, the fabrication of the partial denture dental appliance might require several fittings and adjustments by the dentist and the dental laboratory in order to obtain a secure fit which did not subject the abutment teeth to any undue influence from stress or strain. The past practice required many minor adjustments which when made on one location of the partial denture dental appliance might in fact influence another location on the partial denture dental appliance. Applicant's method ensures the proper fit with little or no subsequent adjustment.

As illustrated in FIG. 1, the individual's lower jaw contains seven (7) adult teeth. In order to secure a partial denture dental appliance to the lower jaw, one or more of the original teeth will have to be crowned in order to provide support for the partial denture dental appliance. The teeth to be crowned in order to provide such support are normally referred to as abutment teeth and for the purposes of illustration, the abutment teeth to be utilized in describing Applicant's method will be tooth 1, tooth 2 and tooth 7. Crowns would be prepared from the impression of the individual's mouth in the normal manner. From the impression, waxed up crowns and/or copings would be prepared and cast in metal. The original abutment teeth, 1, 2 and 7, would be ground down to accept the crown and/or coping. The crown would be cast in metal with a ceramic layering added to that portion of the crown facing outwardly or visible by another individual when the patient's mouth was open. The rear portion of the crown facing interiorly in the patient's mouth would remain a metal surface 8.

As illustrated in FIG. 1, abutment tooth 1 and abutment tooth 2 are adjacent to each other and could be prepared as separate distinct crowns or as a single crown. Either procedure is acceptable to Applicant's method.

Once the crowns have been prepared and fitted onto refractory model 10, the dental laboratory must determine the location for attachment of the partial denture dental appliance. In order to secure a proper fit, Applicant's method identifies a location in which a female recess may be located in order to cooperate with a male aligning plug which would be attached to the dental appliance.

The location for positioning this female recess would normally be in one of three locations with respect to a dental crown. The first location, the distal location, identified by reference letter A, is located on the inside rear portion of the crown. The second location, the mesial location, identified by reference letter B, is located on the inside forward portion of the crown. The third location, the interproximal location, is located between adjoining crowns and identified by reference letter C. With respect to attachment to a coping, the positioning would normally be at the occlusal location.

The choice of location, either distal, mesial or interproximal, is made in order to ensure the securest fit with least amount of stress or strain on the abutment tooth. Once the proper location is determined, the female recess is formed utilizing an EDM machine or electro-discharge machining method machine which utilizes low voltage and low amperage under reversing polarity. The refractory model with the crowns positioned on abutment teeth 1, 2 and 7 would be connected to a first electrode on the EDM machine and submerged in a mineral oil or dilectium solution and aligned with a second electrode which would be brought into contact with the metal surface of the crown or coping and under the influence of reversing polarity, would erode the female recess. For the purposes of the example illustrated in FIG. 1, female recess 16 is located at the mesial location on abutment tooth 7 and female recess 18 is located in the interproximal location between abutment tooth 1 and abutment tooth 2. The preferred method of forming the female recess is by the EDM method. However, an alternative method utilizing a prefabricated plastic form can be utilized in the metal casting step of the crown or coping. Once the crown or coping is set, the plastic form could be removed thus forming the female recess.

Once the female recesses 16 and 18 have been positioned on the crowns of the abutment teeth, a waxed refractory model of the partial denture dental appliance framework is prepared using the lost wax technique. In this method, an impression is taken of the refractory model to obtain an impression of the underlying superstructure of the partial denture dental appliance. This underlying superstructure 20 is illustrated alone in FIG. 2 and in alignment with refractory cast 10 in FIG. 1. The underlying superstructure consists of a pair of saddles 22 and 24 connected by a U-shaped bar 26 which is also known in dental terms as the major connector and a pair of uprights 28 and 30 which extend upwardly from the connecting bar and are known in dental terminology as the minor connectors. The saddles are generally concave in nature and designed to conform to the underlying gum shapes 12 and 14. Connecting bar 26 connects the two saddles and is positioned rearwardly from the front teeth. The uprights or minor connectors 28 and 30 are designed to embrace the abutment teeth.

The dental appliance partial framework is fabricated of any suitable metal. Once it is cast to metal, the electrical discharge machining method is utilized to conform the partial denture dental appliance 20 to the metal surfaces of the crowns on abutment teeth 1, 2 and 7. The partial denture dental appliance is cast to metal and attached to the upper member of the EDM machine. The working model of the mouth impression is attached to the lower member of the EDM machine. The upper member and lower member of the EDM machine are in alignment configuration such that the working refractory model of the mouth and the partial denture dental appliance are in aligning relationship as illustrated in FIG. 1.

The EDM machine is then used to bring the partial denture dental appliance into contact with the working refractory model and, in particular, the metal surfaces of the crowns on abutment teeth 1, 2 and 7 so as to erode the uprights or minor connectors 28 and 30 to the circumferential surface of the crown or coping where it has been undercut in order to ensure a stress-free embrace of the crown by the partial denture dental appliance through the uprights. Additionally, the male plugs 32 and 34 on uprights or minor connectors 28 and 30 are eroded to conform to the female recess which was previously positioned utilizing the electrical discharge machining method.

When the erosion technique is completed, the male plug and female recess of partial denture dental appliance 20 are in alignment and produce a snug fitting and the uprights or minor connectors together with the metal surface of the crowns on abutment teeth 1, 2 and 7 have been eroded such that there is a snap-fit connection which maintains the partial denture dental appliance in position and which does not produce any significant or undue stress or strain factors on the abutment teeth. This is illustrated in FIG. 3.

Once partial denture appliance 20 has been fabricated to engage female recesses 16 and 18 in the abutment teeth 1, 2 and 7, and the uprights or minor connectors 28 and 30 have been eroded to embrace the metal portion of the crowns or copings associated with the abutment teeth, all that remains is for the siliconizing of the partial denture dental appliance and the fabrication of the acrylic replacement teeth for fitting on saddles 22 and 24 as partially illustrated in FIG. 3 which illustrates the positioning of two acrylic teeth 34 and 36 on saddle 22.

Applicant's process has been illustrated with respect to the fabrication of a major partial denture dental appliance which replaces all of the patient's lower molars on both the right and the left. Applicant's process also has application to the fabrication of a partial denture dental appliance which may only replace on either the right or left side of the patient's upper or lower jaw or to a partial denture dental appliance which may be fabricated for replacement of only certain teeth in the patient's right, left, upper or lower jaw, more commonly known as a bridge. In either of the instances, Applicant's utilization of the erosion technique with respect to the manner in which the partial denture dental appliance is secured to an abutment tooth ensures that the stress and strain on the abutment tooth is greatly diminished and thus the possibility of subsequent loosening or loss of the abutment tooth is substantially reduced.

FIG. 4 is a schematic flow chart illustrating the process previously discussed for the fabrication and fitting of the partial denture appliance. While the invention has been described with reference to its preferred embodiment thereof, it will be appreciated by those of ordinary skill in the art that various changes can be made in the process without departing from the basic spirit and scope of the invention.

What is claimed is:

1. A process for the fabrication and fitting of a partial denture or bridge appliance removably securable to abutment teeth having a crown or coping within the individual's mouth, said partial or bridge dental appliance comprising of one or more saddles complimentary to said gum line, a connecting base between said saddles and upright minor connectors for engaging said crown or coping on said abutment teeth, the process comprising:

a. preparing a refractory master cast of a patient's mouth, identifying said patient's permanent teeth and gum line;

b. identifying said abutment teeth for the acceptance of said crown or coping and subsequent abutment tooth preparation by the dentist;

c. preparing said crown or coping for abutment teeth and installing said crown or coping on said abutment teeth;

d. identifying the distal, mesial, interproximal, or occlusal location on the interior portion of said crown or coping for positioning of a securing means for said dental appliance;

e. submersing said refractory master cast and said crown or coping in a mineral oil or dilectium bath;

f. forming a female recess at said selected distal, mesial, interproximal or occlusal location by means of electrical erosion utilizing reversing polarity;

g. removing said refractory master cast from said mineral oil or dilectium bath and preparing a wax pattern of said dental appliance conforming to said abutment teeth, said female recess and said gums of said refractory master cast;

h. casting said dental appliance in metal;

i. connecting said dental appliance to a first electrode and connecting said crown or coping on said refractory master cast to a second electrode of opposite charge;

j. submersing said dental appliance in alignment with said refractory master cast in said mineral oil or dilectium bath;

k. gradually lowering said dental appliance in alignment with said refractory master cast into contact with said crown and coping on said refractory master cast, electrically eroding said dental appliance to form a male plug complimentary with said female recess in said crown or coping and further electrically eroding said minor connectors of said dental appliance to conform to the surface of said crown or coping on said abutment teeth;

l. securing acrylic teeth or porcelain or acrylic resin to said dental appliance.

2. The partial denture or bridge appliance produced by claim 1.

* * * * *